United States Patent
Hermida

(10) Patent No.: US 6,949,525 B2
(45) Date of Patent: *Sep. 27, 2005

(54) USE OF A MIXTURE OF SODIUM HYALURONATE AND CHONDROITIN SULFATE FOR THE TREATMENT OF OSTEOARTHRITIS

(75) Inventor: Elias Humberto Ochoa Hermida, Mexico City (MX)

(73) Assignee: Alcon, Inc., Hunenburg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/469,258
(22) PCT Filed: Nov. 13, 2002
(86) PCT No.: PCT/EP02/12703
  § 371 (c)(1),
  (2), (4) Date: Aug. 27, 2003
(87) PCT Pub. No.: WO03/041724
  PCT Pub. Date: May 22, 2003

(65) Prior Publication Data
  US 2004/0082540 A1 Apr. 29, 2004

(51) Int. Cl.$^7$ ............................................. A61K 31/715
(52) U.S. Cl. ....................................................... 514/54
(58) Field of Search ........................................... 514/54

(56) References Cited

U.S. PATENT DOCUMENTS

| 4,636,524 A | 1/1987 | Balazs et al. |
| 4,713,448 A | 12/1987 | Balazs et al. |
| 5,099,013 A | 3/1992 | Balazs et al. |
| 5,143,724 A | 9/1992 | Leshchiner et al. |
| 5,409,904 A | 4/1995 | Hecht et al. |
| 5,498,606 A | 3/1996 | Soll et al. |
| 5,929,050 A | 7/1999 | Petito |

FOREIGN PATENT DOCUMENTS

| EP | 0 875 248 A1 | 11/1998 |
| WO | WO 96/32929 | 10/1996 |
| WO | WO 00/44367 | 8/2000 |

OTHER PUBLICATIONS

Brown et al., "Gelatin/Chondroitin 6–Sulftae Microspheres for the Delivery of Therapeutic Proteins to the Joints," *Arthritis & Rheumatism*, 41(12):2185–2195 (Dec. 1998).
Buckwalter et al., "The Increasing Need for Nonoperative Treatment of Patients with Osteoarthritis," *Clinical Orthopaedics and Related Research*, 385:36–45 (2001).
Hardingham, "Chondroitin Sulfate and Joint Disease," *Osteoarthritis and Cartilage*, 6 (Suppl A): 3–5 (1998).
Nerucci et al., "Effects of chondroitin sulfate and interleukin–1β on human chondrocyte cultures exposed to pressurization: a biochemical and morphological study," *Osteoarthritis and Cartilage* 8:279–287 (2000).
Watanabe et al., "Roles of Aggrecan, a Large Chondroitin Sulfate Proteoglycan, in Cartilage Structure and Function," *J. Biochem* 124:687–693 (1998).

*Primary Examiner*—James O. Wilson
*Assistant Examiner*—Ganapathy Krishnan
(74) *Attorney, Agent, or Firm*—Barry L. Copeland

(57) ABSTRACT

This invention is related to the use of the composition formed by sodium hyaluronate and sodium chondroitin sulfate for the treatment of chondral lesions in osteoarthritis, and to the use of such composition in the manufacture of a product for such treatment.

16 Claims, 15 Drawing Sheets

USE OF A MIXTURE OF SODIUM HYALURONATE AND CHONDROITIN SULFATE FOR THE TREATMENT OF OSTEOARTHRITIS

This is a U.S. national application under 35 U.S.C. §371 of PCT/EP02/12703 filed Nov. 13, 2002.

FIELD OF THE INVENTION

This invention is related to methods and compositions for the treatment of arthritis, and in particular the treatment of osteochondral lesions associated with osteoarthritis by means of the intraarticular application of a mixture of hyaluronate and chondroitin sulfate.

Specifically, this discovery has its preferred application in the lubrication and regeneration of the articular cartilage damaged by grade I and grade II osteoarthritis of human or animal (preferably mammalian) joints including without limitation the knee, shoulder, sacroiliac, hip, ankle, elbow, interphalangeal and wrist joints through the intraarticular application of a mixture of sodium hyaluronate and chondroitin sulfate in gel.

The main objectives of the invention are to introduce the new medical use of the mixture of sodium hyaluronate and sodium chondroitin sulfate for the regeneration of articular cartilage damaged by osteoarthritis, corresponding treatment regimens, and the use of the components in the manufacture of products for such therapies.

BACKGROUND OF THE INVENTION

Osteoarthritis is a condition that affects many millions of persons throughout the world. Previously, there has been no effective treatment that specifically targets the chondral lesion associated with the condition and promotes the in situ regeneration of cartilage at that site.

This disease consists of the gradual degeneration and destruction of the articular cartilage due to traumas, structural deformities of the joints, and overweight. This process thins the cartilage through a phenomenon called apoptosis, or programed cell death. When the surface area has disappeared due to the thinning, it is considered grade I osteoarthritis; when the tangential surface area has also disappeared, it is characterized as grade II osteoarthritis. There are other levels of degeneration and destruction, which affect the deep and the calcified layers that border with the subchondral bone.

The clinical manifestations of the development of the condition are: swelling of the joint, pain, crepitation and functional disability that, gradually and steadily, hinders physical mobility, e.g. the taking of lengthy walks and, depending on the affected joint, forced flexion and extension movements. As the condition worsens, pain begins to limit even minimum efforts and can persist at rest making it difficult to sleep. If the condition persists without correction and/or therapy, the joint is totally destroyed, leading the patient to major replacement surgery with total prosthesis, or to disability.

Therapeutic methods for the correction of the articular cartilage lesions that appear during the osteoarthritic disease have been developed, but so far none of them have been able to achieve the regeneration of articular cartilage in situ and in vivo.

The prior art methods include the following:

a) The application of tendinous, periosteal, fascial, muscular or perichondral grafts.

b) The implantation of fibrin or cultured chondrocytes (Osteochondral Grafts Improve Symptoms but May Increase Risk. Of Ostteoarthritis, medscape.com/con/2000/AAOS/story.cfm).

c) The administration of chondrogenic stimulating factors such as "insulin-like growth factors I and TGF-B".

d) Implantation of synthetic matrices, such as collagen and carbon fiber.

e) Others, such as electromagnetic fields. (J. Buckwalter, M.D., Van C. Mow, Ph. D. and Anthony Ratcliffe, Ph.D. Journal of the American Academy of Orthopaedic Surgery 1994; 2:192–202). All of these have reported minimal and incomplete results with formation of repair, but not regenerative tissue, resulting in a poor quality tissue that can neither support the weighted load nor allow the restoration of an articular function with normal movement.

One treatment that has 74% to 90% effectiveness and produces excellent results, similar to that presented in this invention, is the transplantation of cultured autologous chondrocytes. This method of treatment was first reported in 1987 in Sweden and was introduced in 1995 to the United States of America. It consists of taking chondral cellular material from the patient, sending it to a laboratory where it is seeded in a proper medium for its proliferation, and then, once enough volume is achieved (a variable period that may last from weeks to months), transporting it in a special container, and finally implanting it in the damaged tissues to cover their defects. This is an expensive procedure that requires the patient to be in the operating room for the removal of the necessary cellular material, and subsequently for the implantation of the proliferated material. Furthermore, a significant waiting period is needed for the implant to be ready (VLADIMIR, Bobic, MD AAOS Annual Meeting, Mar. 16, 2000.)

Other, more conventional treatments include antiinflamatories, antirheumatics, systemics, physiotherapy, injection of depot steroids and, recently, viscoprotection has emerged.

Viscoprotection involves the intraarticular application of commercially available sodium hyaluronate viscoelastic materials such as HYLAN G-F 20, SYNVISC, HYALGAN, ARTZ, etc. The sodium hyaluronate substance does affect the rheology of the synovial fluid, producing an almost immediate sensation of free movement and a marked reduction of pain. It has been proven that the change of the intraarticular fluids attendant to sodium hyaluronate instillation produces a blockage of the nociceptors of subsynovial and capsular tissues and that, in addition to the mechanical factors of the osteochondral pathology, the fluids influence these receptors with their lubricating properties. Thus the change in viscosity of these fluids acts favorably on the painful osteochondral symptoms when sodium hyaluronate is instilled. However, the effect of conventional hyaluronate is temporary because the material remains within the articular chamber for only about 72 hours before it is absorbed and/or metabolized. The residual effects of this substance act on the synovial receptors causing a pain reduction that lasts several weeks and even months. However, this isolated effect is counterproductive for the course of the disease and for the viability of the cartilage because, as it masks the symptoms, the joint is used with more intensity and its destruction is accelerated as the original problem is not corrected and the damaged articular cartilage is not restored. Recent studies with a 5 year follow-up with these substances indicate that clinical improvement is significant and that is represents a remission factor of painful symptoms, but only for short and medium term. Also, adverse effects, characterized by severe pain, significant synovial effusion, rash and ankle edema, have been reported in at least 7.2% of the treated patients. In no instance has hyaluronate therapy been reported to effect cartilage regeneration and long term success. The need exists, therefore, for an improved approach to cartilage regeneration.

As an antecedent to this invention, in 1982, the applicant began applying sodium hyaluronate (SH) to thoroughbred race horses at Hipódromo de las Américas (Las Américas Race Track), in Mexico City, Mexico. The knees and ankles are the most commonly injured joints in these horses. Veterinarians at racetracks in the USA had already used this procedure, observing the beneficial reaction that this viscoelastic material produced in the injured knees of the horses. The applicant considered its use in humans, and conceived of adding some substance to cause the restoration of the damaged surface of the cartilage.

The applicant hypothesized that chondroitin sulfate (CS), the most important part of the aggrecan proteglycans which are the basis of chondral support, might have a repaving effect.

In 1996 while visiting Alcon Laboratories in Mexico City, the applicant learned that one of the company's ophthalmic products contained both of the above mentioned substances in a gel suspension (VISCOAT®). The inventor obtained detailed information, including the product monograph for VISCOAT® that states that is has no reported side effects in introacular use; furthermore, there are ample references from efficacy and safety studies of this product (CILCO, In. Summary of safety and efficacy for Viscoat, 1984). It was then that the applicant decided to use it experimentally in patients with osteoarthritis disorders of all degrees, and subsequently analyze the results.

The present study reveals another alternative in the management of osteochondral lesions of the knee through the intraarticular application of a mixture of sodium hyaluronate and sodium chondroitin sulfate. While bound by no theories, it may be that the remarkable effectiveness of this therapy is attributable to the promotion of chondrogenesis synergistically combined with the known benefits of viscoelastic therapy. Implanting an artificial matrix of chondroitin sulfate and sodium hyaluronate may represent an indispensable repair factor, as in it naturally arising chondrocytes can proliferate and restore the continuity of the tissue, regenerating the destroyed cartilage to its original form.

With this matrix, the symptomatic evolution is significantly favorable and long lasting due to the regeneration of cartilage at the chondral lesions. No side effect have been reported except in a patient who reported pain and slight swelling at the site of application, which subsided spontaneously in 24 hours; he was given acetaminophen as an analgesic.

It must be pointed out that in the most preferred usage the product is administered exactly as it is presented for intraocular use and no change is made in the formulation. A change in presentation with a larger capacity syringe is now being proposed, as the current ophthalmic presentation has 0.5 c.c. and 0.75 c.c. syringes.

It must also be pointed out that although this is the same preparation as that used intraocularly, its use for this purpose is totally different as it is applied in a conventional intraaticular manner as an inductor of chondrogenesis, to regenerate the cartilage destroyed by osteoarthritis.

As previously mentioned, experimental application of this composition in humans started in 1996, and excellent results have been noted. These were confirmed later by arthorscopic studies (direct view of the articular cartilage through the insertion of a camera into the joint), pathological anatomy and histophysiological studies, all of them consistent with the clinical findings that the regeneration of normal articular cartilage was achieved. This is why this treatment is presented as the only currently available procedure that can offer up to 955 regeneration of articular cartilage damaged by grade I and II osteoarthritis in any joint of the human body.

SUMMARY OF THE INVENTION

This invention was developed to solve the problem of the previously available techniques related to the treatment of articular cartilage damaged by osteoarthritis.

This invention introduces a method to achieve regeneration of the articular cartilage by chondrogenic induction through the intraarticular implantation of an artificial matrix in patients and animals with chondromalacia and/or osteoarthritis in any joint, but preferably in human patients with grade I or II osteoarthritis.

The regeneration process is elicited by implanting an artificial matrix formed by a mixture of chondroitin sulfate and hyaluronic acid or pharmaceutically acceptable salts thereof, where naturally arising chondrocytes can settle, and where, as they mature, they form, in groups of 3 or 4, their own definitive hyaline matrix, duplicating the same pattern of the natural cartilage. In this manner the continuity of the articular surface is recovered, mobility is regained, pain is eliminated and thus function is recovered.

BRIEF DESCRIPTION OF THE DRAWINGS

FIGS. 1 and 2 represent pre- and two years posttreatment arthroscopic images, respectively.

FIG. 3 represents the regeneration of the articular cartilage with De Novo cartilage.

FIGS. 4 and 5 are microscopic images that show the maturing of the zone tangential of the superficial layer where fully developed and maturing chondrocytes are found, surrounded by a hyaline matrix.

FIG. 6 is a confirmatory histophysiological image with the application of S-100 protein. It shows the reaction of the cartilaginous tissue to this test with a positive result.

CHARACTERISTICS OF THE PRODUCT

Figure 1:
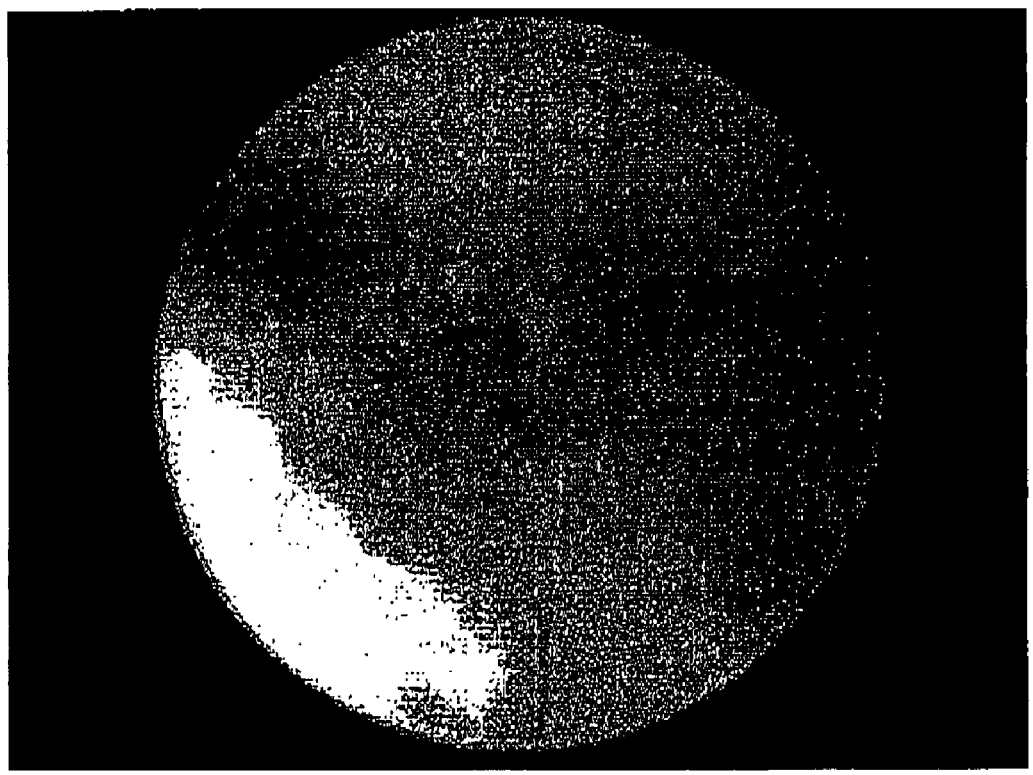
FIGS. 1 to 6 represent pre- and postimplantation arthroscopic images from patients who underwent the treatment of the present invention: macro and microscopic confirmation of regeneration of the articular surface with De Novo cartilage with the same characteristics as the original, a conclusive pathology report, and histophysiology tests (S-100 Protein) both of which confirm the characteristics of the regenerated cartilage.
Figure 2:
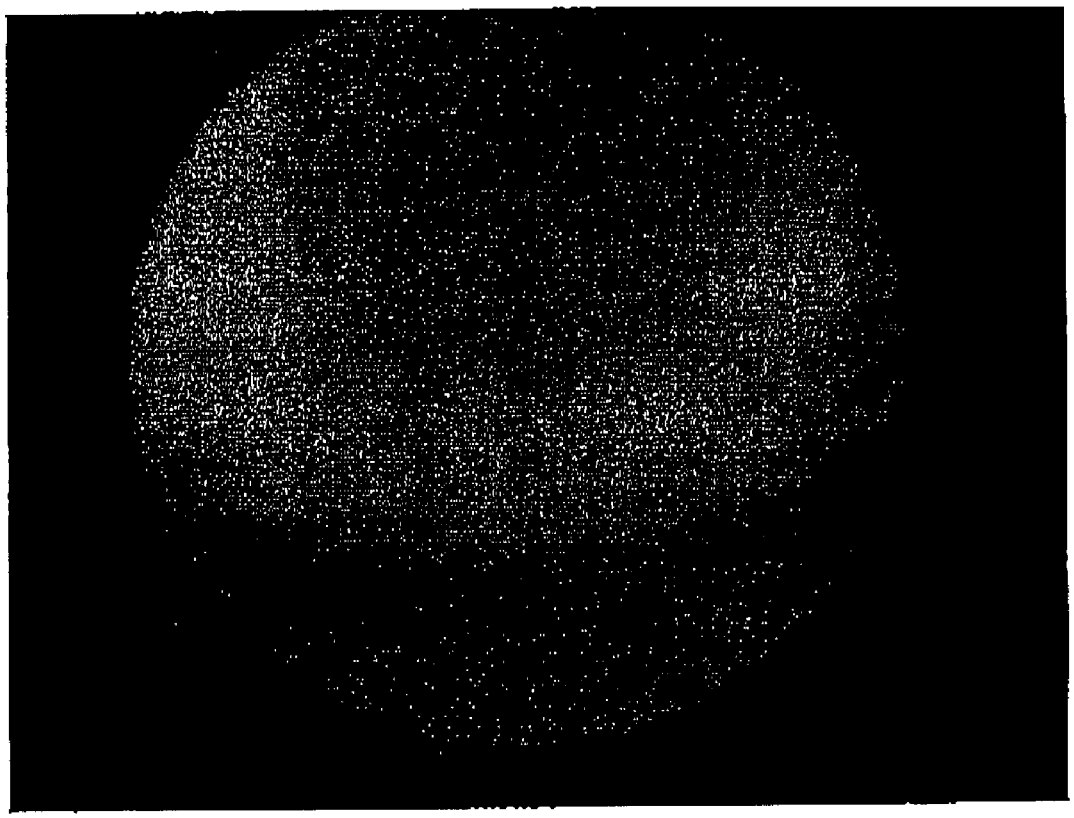

In its preferred embodiment, the chondroitin sulfate/hyaluronate composition of the present invention is presented under the trade name of VISCOAT® (Alcon Laboratories, Inc., Fort Worth, Tex., USA). It is osteoarthritis (OA) in patients, and particularly in those who fail to respond adequately to traditional non-drug therapies and plain analgesics.

The VISCOAT® product packaging identifies U.S. Pat. Nos. 4,486,416 and 6,051,560, the entire contents of both of which are by this reference incorporated herein. The VIS- COAT® product is also registered before the SSA (Mexican Health Secretariat) under registration number Reg SSA Mex. No 0735 C 88.

According to the manufacturer provided product information:

"VISCOAT® Viscoelastic Solution is a sterile, non-pyrogenic, viscoelastic solution of highly purified, non-inflammatory medium molecular weight sodium chondroitin sulfate and sodium hyaluroante. VISCOAT® is formulated to a viscosity of 40,000±20,000 cps (at shear rate of 2 $sec^{-1}$, 25° C.). Each 1 mL of VISCOAT® solution contains not more than 40 mg sodium chondroitin sulfate, 30 mg sodium hyaluronate, 0.45 mg monobasic sodium phosphate, monohydrate, 2.00 mg diabasic sodium phosphate anhydrous, 4.3 mg sodium chloride (with Water For Injection, USP grade, q.s.). The osmolarity of VISCOAT® is 325 mOsM±40 mOsM; the pH is 7.2±0.2.

Sodium chondroitin sulfate and sodium hyaluronate are quite similar in regard to chemical and physical composition, as each occurs as a large, unbranched chain structure of medium to high molecular weight. The sodium chondroitin sulfate used in the preparation of the VISCOAT® Viscoelastic Solution has a mean molecular weight of approximately 22,500 daltons, while the sodium hyaluronate exhibits a molecular weight of over 500,000 daltons."

This product has a gel presentation that contains a mixture of sodium hyaluronate and chondroitin sulfate; these substances exist in natural form in the human body as part of cartilage, synovial membrane, umbilical cord and vitreous humor of the eye.

DETAILED DESCRIPTION OF THE INVENTION

The product is applied or instilled by conventional intraarticular means, typically injection, with prior asepsis and antisepsis of the region. This is typically done in the treatment room of the physician's office. The product applied (injected) is called an implant. As previously explained, CS is the most important part of aggrecan, a predominant proteoglycan in articular cartilage. The CS acts with its long chains inserted in the protein nucleus as a support element of the chondral stroma. It is thus that it serves as an artificial matrix that sticks to the bed of the lesion, allowing the migrating, unattached, peripheral chondrocytes of the erosion to settle in it. When they mature, the chondrocytes secrete a definitive hyaline matrix that replaces the temporary one afforded by the viscoelastic composition ("wet nurse") and thus it regenerates until it manages to recover the original shape and thickness. This has been verified when, upon performing controlled post-implant arthroscopy, cartilage regeneration is observed macroscopically. Microscopically, findings of "De Novo" articular cartilage with normal morphological characteristics, as well as positive histophysiological results to S-100 protein, are reported.

The preferred method for this invention's chondrogenic induction is the intraarticular application of a mixture containing 60 mg of CS and 45 mg of SH in a gel suspension, equivalent to 1.5 c.c. of the formulation, when dealing with large joints, and the preferred application of a mixture containing 30 mg of CS and 22.5 of SH in 0.75 cubic centimeters for smaller joints such as the coxofemoral, ankle or elbow joints. The inventor has also determined that for even smaller joints such as the interphalangeal or wrist joints, a mixture containing 20 mg of CS and 15 mg of SH in 0.5 cubic centimeters be used. The number and frequency of administration of the doses of the composition will be similar to those used in conventional viscoprotective therapy regimens, and will be adjusted to suit the needs of the particular patient. Generally, 2 to 6 doses are administered over 1 to 3 months. 2–4 doses administered at 10–20 day intervals are preferred. Most preferred is a regimen of 3 doses at 15 day intervals with subsequent periodic applications every 3, 6, 9, or 12 months, depending on the results. This method produces up to a 94.5% regeneration of the articular cartilage destroyed by grade I and II osteoarthritis, according to the results obtained in the study made on 325 knees and 16 coxofemoral joints.

DETAILED DESCRIPTION OF THE COMPOUND USED IN THE TREATMENT

As mentioned previously, it is important to consider that in the most preferred embodiment of the present invention, the product is applied exactly as it is presented for intraocular use, without any changes in the formulation, using a syringe of adequate capacity, for example, a 21×32 sterile hypodermic needle. Concentrations of the chondroitin sulfate and hyaluronate useful for purposes of the invention, however, may range from about 0.15 to about 50% by weight for each such component. The molecular weight of the chondroitin sulfate should be greater than about 20,000 daltons, and preferably between about 20,000 and 50,000 daltons. The molecular weight of the hyaluronate should be at least 500,000 daltons and preferably between about 500,000 and 1,000,000 daltons.

In the practice of the invention, sodium hyaluronate may be used at concentrations from about 0.1 g up to about 10 g in 100 ml water at temperatures between about 4° c. and about 37° C. Chondroitin sulfate is also used at concentrations from about 0.1 g up to about 10 g in 100 ml water at temperatures between about 4° C. and about 37° C. Other pharmaceutically acceptable salts, including without limitation magnesium, calcium and potassium chondroitin sulfates and hyaluronates are also useful in the practice of the invention. Within the ranges just described, any quantity of chondroitin sulfate can be added to form binding interaction with hyaluronate and produce physical and flow properties suitable for intraarticular uses. Adding 12.6 g of chondroitin sulfate to 10 g sodium hyaluronate in water, the resulting solution has viscosity of over 1 million centipoises at 25° C. for low shear rate below 50 $sec^{-1}$). The preferred ratio of chondroitin sulfate to hyaluronate is about 4:3 by weight. Preferred concentrations range from about 0.1% to about 5.3% by weight for the chondroitin sulfate component and from about 0.1% to about 4.2% by weight for the hyaluronate component.

The preferred aqueous buffer solution used in the practice of the invention includes monobasic sodium phosphate, dibasic sodium phosphate, and sodium chloride mixed to form an aqueous buffer to maintain pH of about 7 to about 8.0 and osmolarity of 300–350 mOsmol/kg. By raising the buffer concentrations of monobasic sodium phosphate and disbasic sodium phosphate, the ionic strength of chondroitin sulfate/hyaluronate solution is increased. The kinetic rate constant of molecule interaction between chondroitin sulfate and hyaluronate is increased by raising ionic strength and temperature. This invention comprises concentrations of dibasic sodium phosphate and monobasic sodium phosphate from 0.1 g/100 ml to 5 g/100 ml and pH range of 7.0 to 8.0 at reaction temperatures between 4° C. and 40° C. The following example shows the effect of buffer on the viscosity or apparent molecular weight of the mixture for 5.3 g CS/4.2 g SH in 100 ml water:

Buffer 1:

Diabasic sodium phosphate: 4.5 mg/ml Sodium dihydrogen phosphate hydrate: 1.5 mg/ml Viscosity of composition of the present invention at 1 $sec^{-1}$ and 25° C. is 68,878 cps.

Buffer 2:

Dibasic sodium phosphate: 7.5 mg/ml Sodium dihydrogen phosphate hydrate: 1.0 mg/ml Viscosity of compositions of the present invention at 1 $sec^{-1}$ and 25° C. is 115,011 cps.

In a most preferred formulations, i.e. the VISCOAT® formulation, each cubic centimeter of the mixture contains 40 mg of chondroitin sulfate (molecular weight of approximately 22,500 daltons), 30 mg of sodium hyaluronate (molecular weight of approximately 750,000 daltons), 0.45 mg of sodium monobasic monohydrate phosphate, 2 mg of sodium dibasic anhydrous phosphate, 4.3 mg of sodium chloride and water.

TESTS PERFORMED

TYPE OF STUDIES: Prospective, longitudinal and xperimental.

A study was conducted on 210 patients, 325 knees with chondromalacia and grades I and II osteoarthritis and 16 joints (coxofemoral) with painful articular symptoms and functional limitation, treated previously in a conventional manner with NSAIDs or with steroid injections; the patients were refractory to these tretments.

INCLUSION CRITERIA

The inclusion criteria during this study were as follows:

Patients of both sexes with chronic chondral or osteochondral pathology of the knee and coxofemoral joint up to grade II arthrosis were included, who had no clinical improvement with conventional treatment, no added autoimmune or neoplastic pathologies, of all ages, with prior arthroscopic surgery, without recent management with systemic or articular steroids or nonsteroidal antiinflammatories (NSAIDs).

EXCLUSION CRITERIA

The following exclusion criteria were adopted: patients with grade III or upper gonarthrosis or coxarthosis, recent or current treatment with systemic or intraarticular steroids, sever deformities and autoimmune or neoplastic pathology.

NON-INCLUSION CRITERIA

Dropping out of treatment, death, change of medical therapy.

The clinical assessment was as follows:

Pain: slight, moderate or sever.

Gait: occasional claudication, assistance with walking stick or crutches or impossible to walk.

Mobility: complete arches, slight, moderate or severe limitation.

Synovial effusion: minimum, moderate or severe (occasional or constant). (SCRIPPS SCALE FOR SPECIAL SURGERY)

Radiographic Assessment:

Radiographic, changes, articular clamping, chondromalacia and osteoarthritis. Pre- and posttreatment radiographic studies.

Arthroscopic Assessment:

Pre- and posttreatment images.

RESULTS 210 patients were treated; 325 knees (115 bilateral (230 knees) and 95 unilateral (95 knees), 144 women (68.5%), 66 men (31.5%), aged 12 to 86 years, a mean of 44.2 years, 48 knees were diagnosed with chondromalacia, 40 with grade I osteoarthritis and 237 with grade II osteoarthritis.

Another 16 patients treated: 16 coxofemoral (hip) joints.

Figure 7:
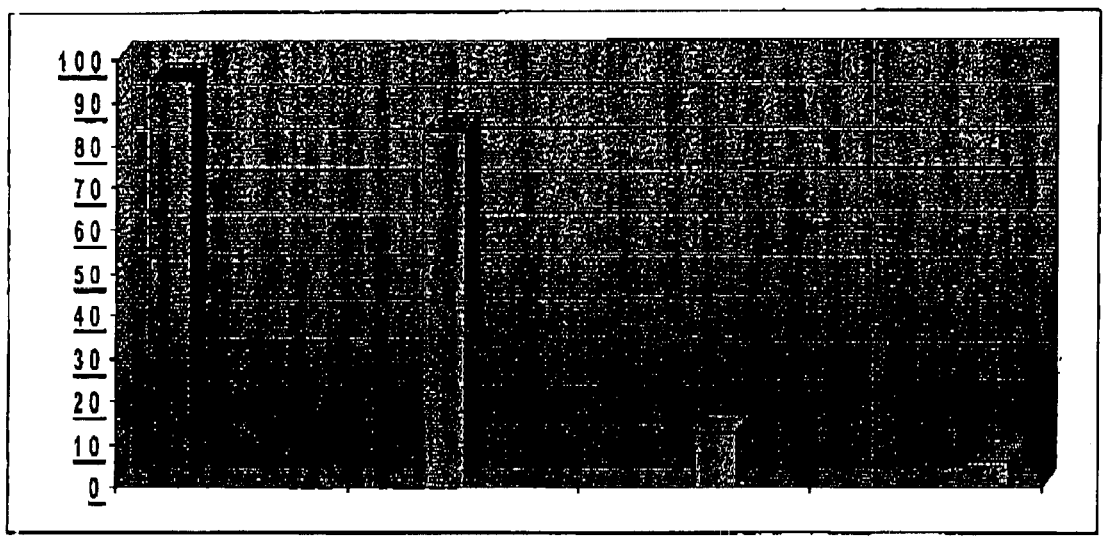
FIGS. 7 to 15 show the graphical results of the studies conducted and described herein.

A visual analog clinical scale (SCRIPPS CLINIC FOR SPECIAL SURGERY) was applied and, as shown in FIG. 7, 309 knees (95.07%) showed immediate significant improvement and satisfactory evolution for up to two years of follow-up, 250 knees (83.3%) remained in the same good conditions without needing to take any NSAID for up to 50 months of follow up, 32 knees (13%) showed moderate pain and 18 cases (6%) showed no short and medium term improvement. Finally, from 16 osteoarthritis coxofemoral (grades I, II, III and IV) (hip) joints, 14 (87.5%) grade I and II coxofemoral joints showed excellent results, and 2 ( 12.5%) grade III and IV coxofemoral joints, due to the advanced degree of deterioration, did not obtain any positive results.

None of the patients had any systemic reactions during this treatment: only one patient reported pain and a slight swelling after the implantation.

Figure 8:
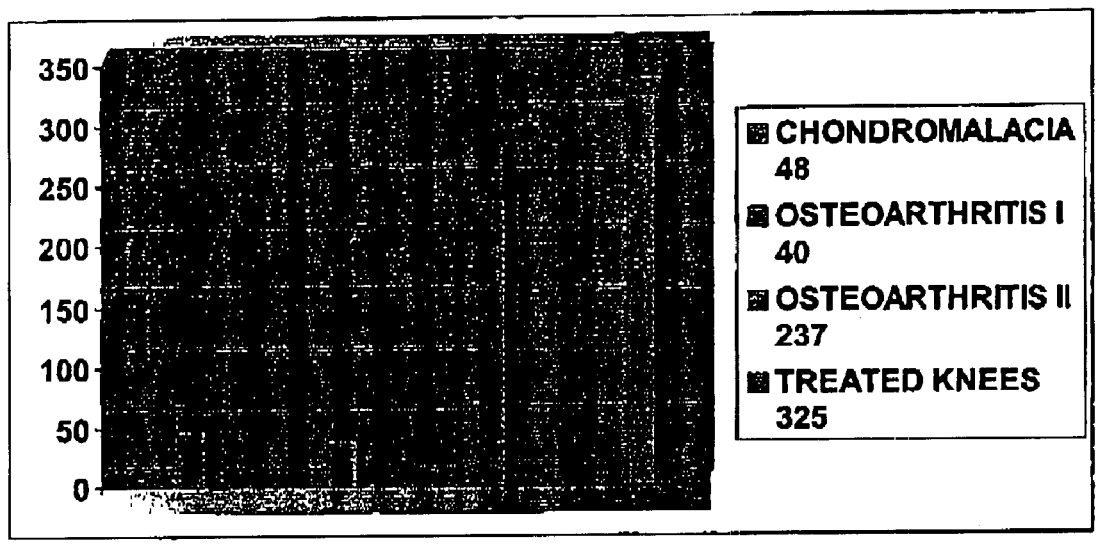
Figure 9:
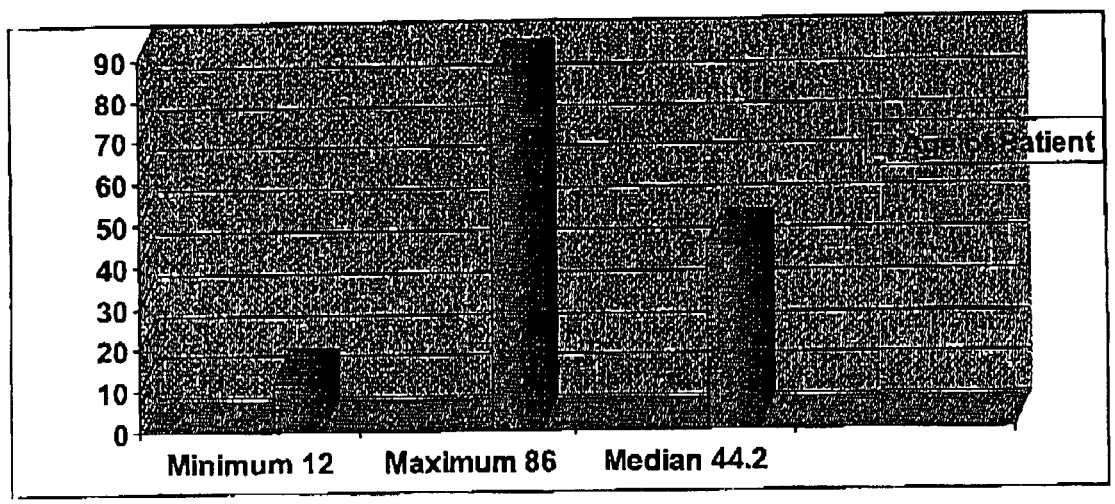
Figure 10:
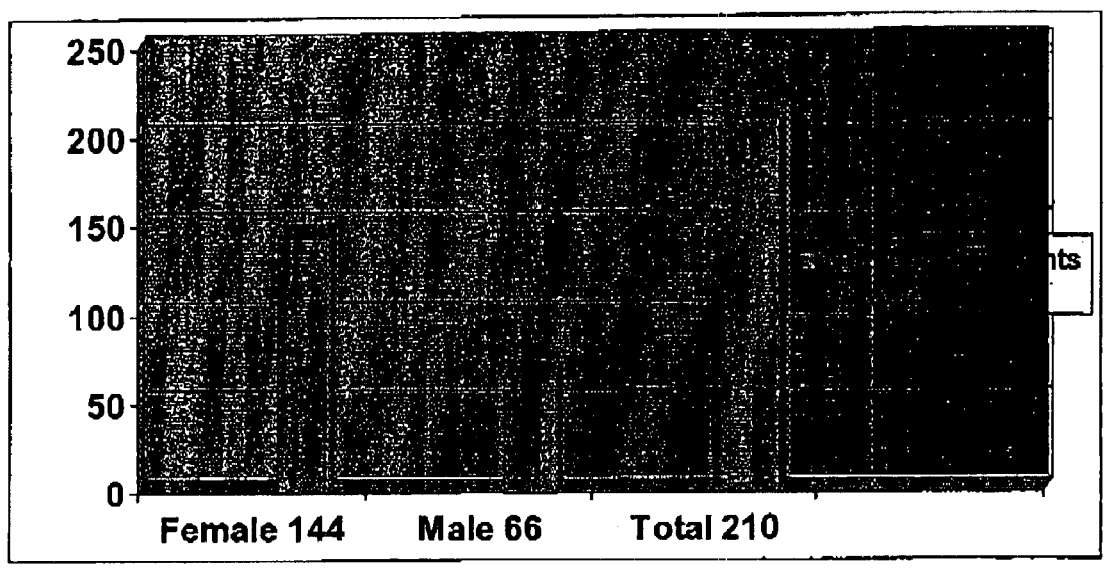

FIGS. 8–10 show the previously described results.

Figure 11:
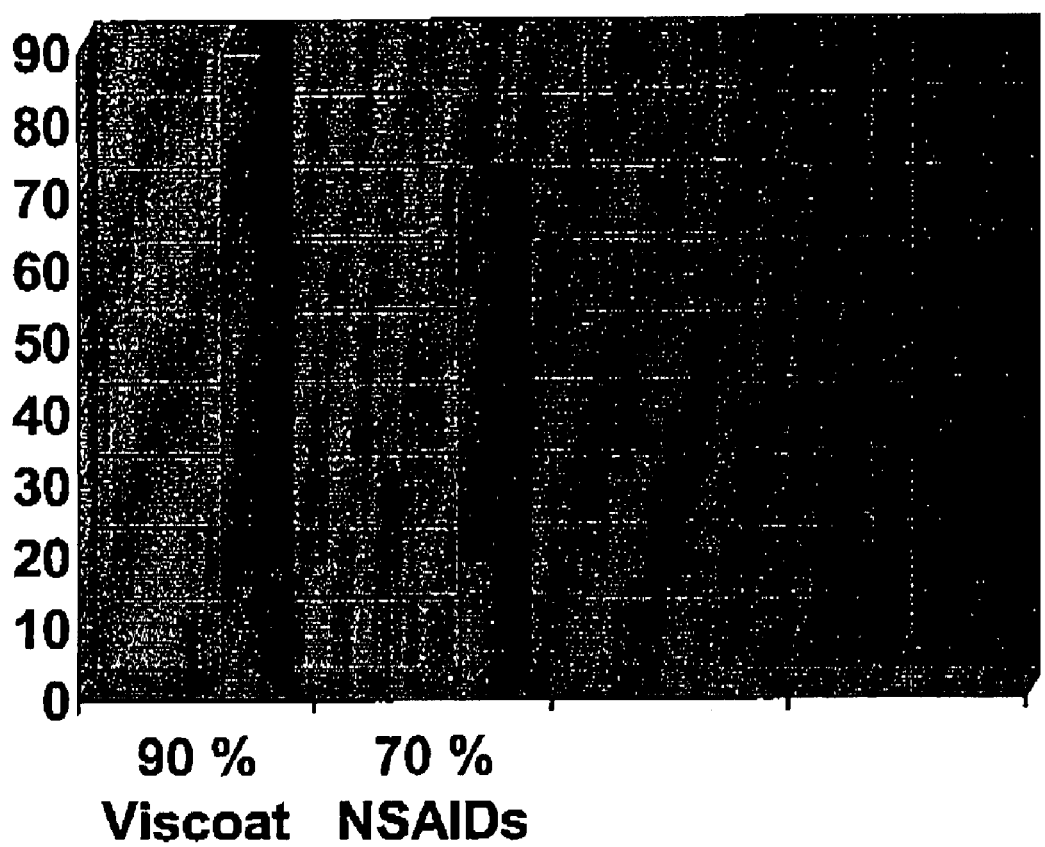
Figure 12:
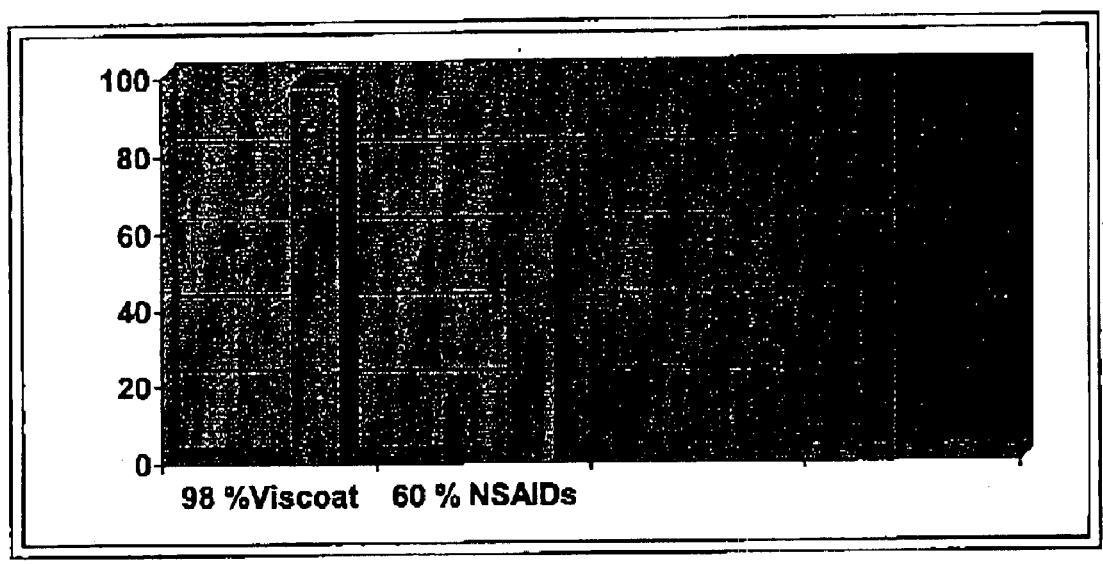

To complement the previous results, a comparative study was conducted on 20 patients treated with NSAIDs due to grade II knee osteoarthritis and 20 patients treated with VISCOAT® for the same reason. The results, after 90 days, were as shown in FIGS. 11 and 12. FIG. 11 shows the results for pain reduction and FIG. 12 the results for increased mobility, each after 90 days.

Figure 13:
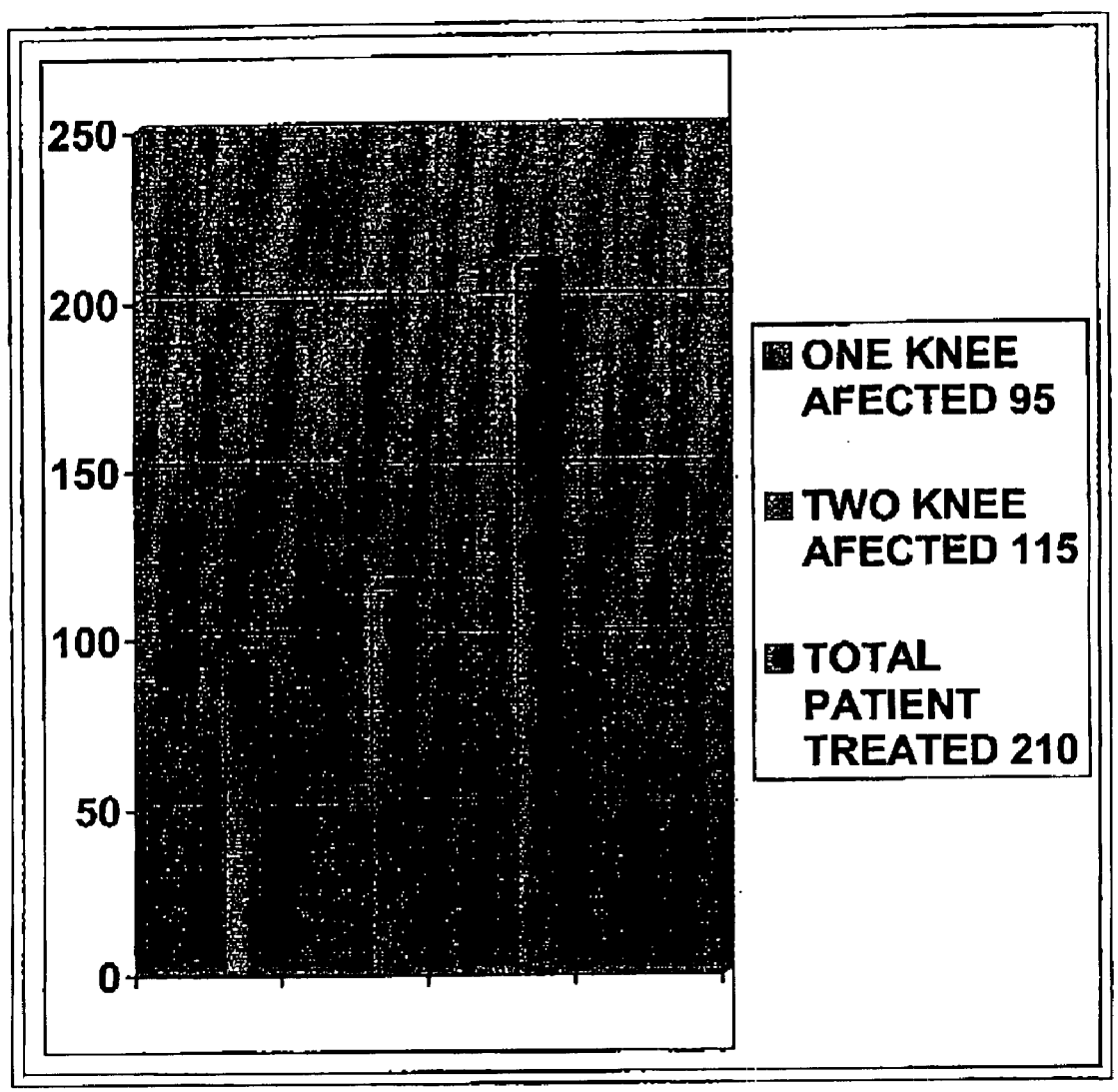

FIG. 13 shows the results after 25 months according to the HSS scale (Scripps Clinics).

DOSES APPLIED

Figure 14:
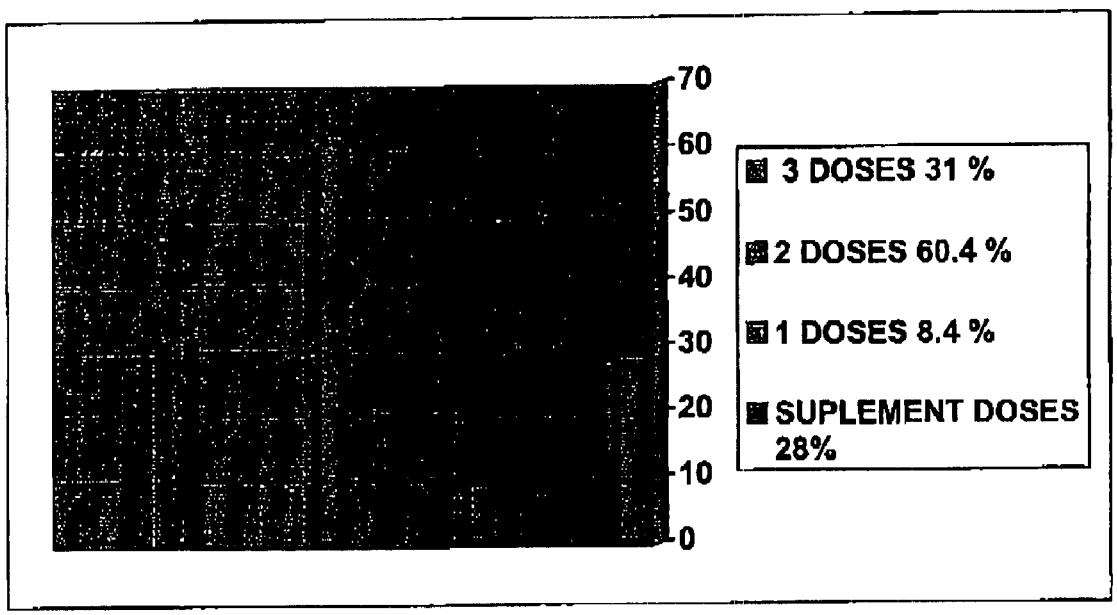

The study continued, as shown in FIG. 14, with the application of 3 doses of the composition to 78 knees, which represented 31% of the knees treated; 151 knees received 2 doses which represented 60.4% and 21 knees received only one dose which represented 8.4%. The 28% shown in the graph of FIG. 14 corresponds to 70 patients who, after 6 months, needed up to 8 supplementary doses; this has reduced the index of nocturnal pain, gait pain and pain at rest, and increased the range of mobility.

Figure 15:
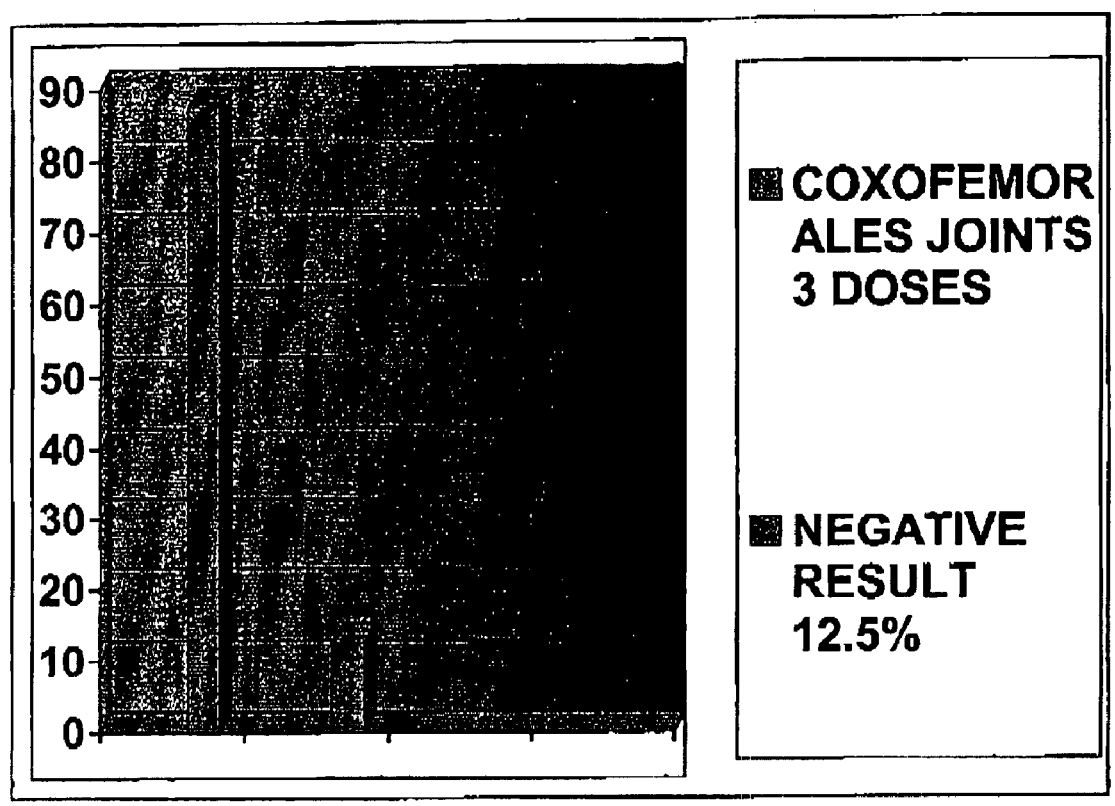

FIG. 15 shows the graphic results of 16 coxofemoral joints, 3 doses covered 87.5% with excellent results in 14 coxofemoral joints treated with the composition, and the 12.5% shown in the graph of FIG. 15 corresponds to the 2 patients with grade III and IV osteoarthritis who did not report any positive results.

These applications were made in 9 male and 7 female patients aged 27 to 79 years.

STUDIES AND TESTS PERFORMED ON PATIENTS THAT PROVE CARTILAGE REGENERATION BY THE APPLICATION OF THE COMPOSITION THAT CONTAINS CS AND SH.

The following examples are given to illustrate and demonstrate the new use of the composition of this invention.

°69 year old female patient treated previously with the composition of sodium hyaluronate and chondroitin sulfate. Biopsy of knee cartilage.

MICROSCOPIC DESCRIPTION:

A histological study of knee cartilage was performed. Its microscopic description was as follows: the sections present fragments of mature cartilage with islands of chondrocyte arranged regularly in groups of 2 to 3, with cohesiveness, and surrounded by a hyaline matrix without laminar fibrosis. The chondrocytes have a round nucleus, clear cytoplasm, and they are morphologically normal and with good maturation. There is no endochondral ossification or dystrophic calcification and, as in the previous example, there is no evidence of malignant neoplasia.

Diagnosis: Biopsy of knee cartilage.

De Novo cartilage formation, morphologically and architecturally normal.

Figure 3:
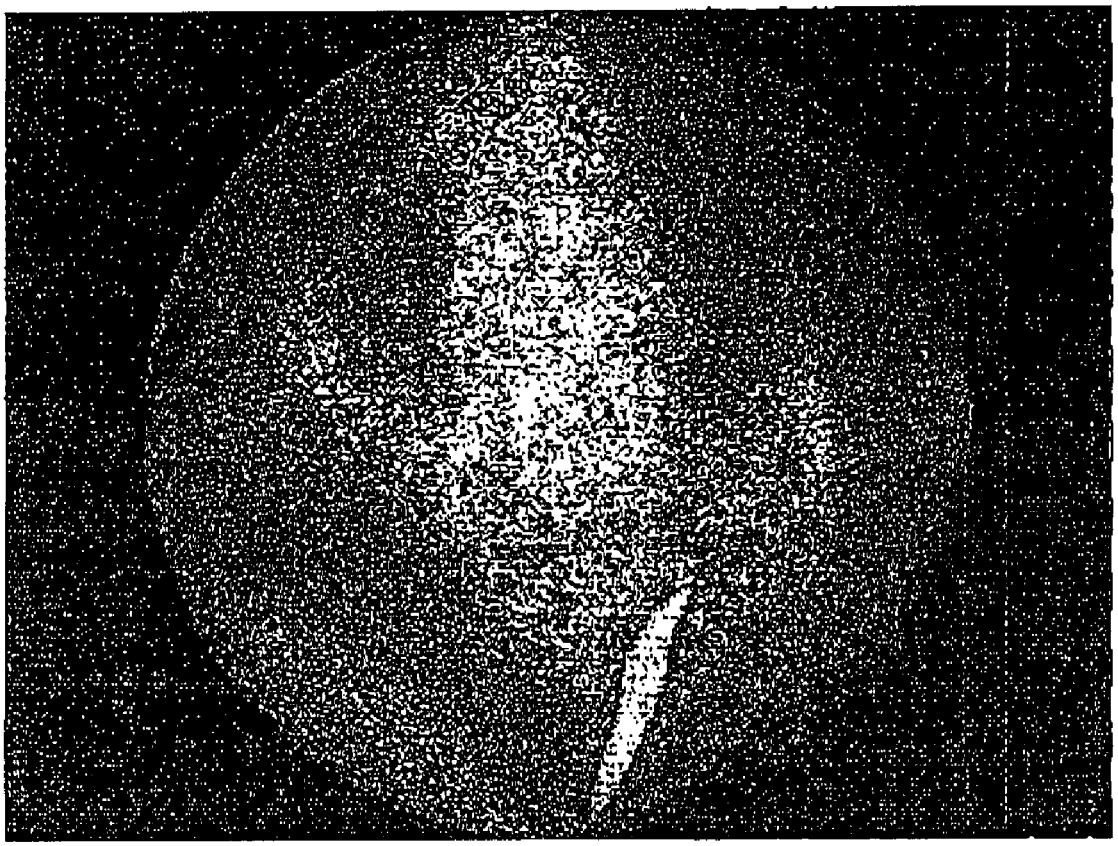

This is confirmed by the image in FIG. 3.

°78-year old female patient treated previously with the compound of sodium hyaluronate and chondroitin sulfate. Biopsy of the femoral condylar cartilage.

Microscopic description:

A histologic study was made of several irregular tissue fragments that jointly measured 0.5 cm; they had a white pearly color, a firm consistency; they were identified as right and left. Parafin technique inclusions were made of them.

Diagnosis: biopsy of femur condylar cartilage.

Figure 4:
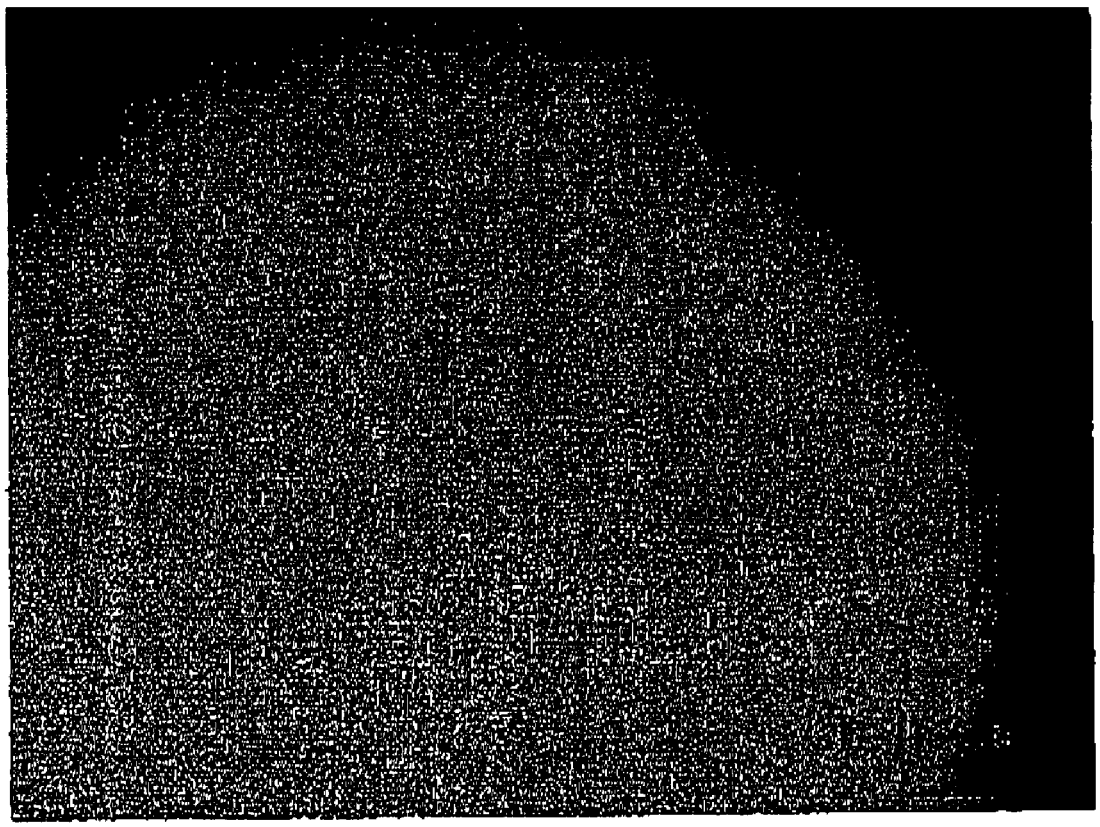
Figure 5:
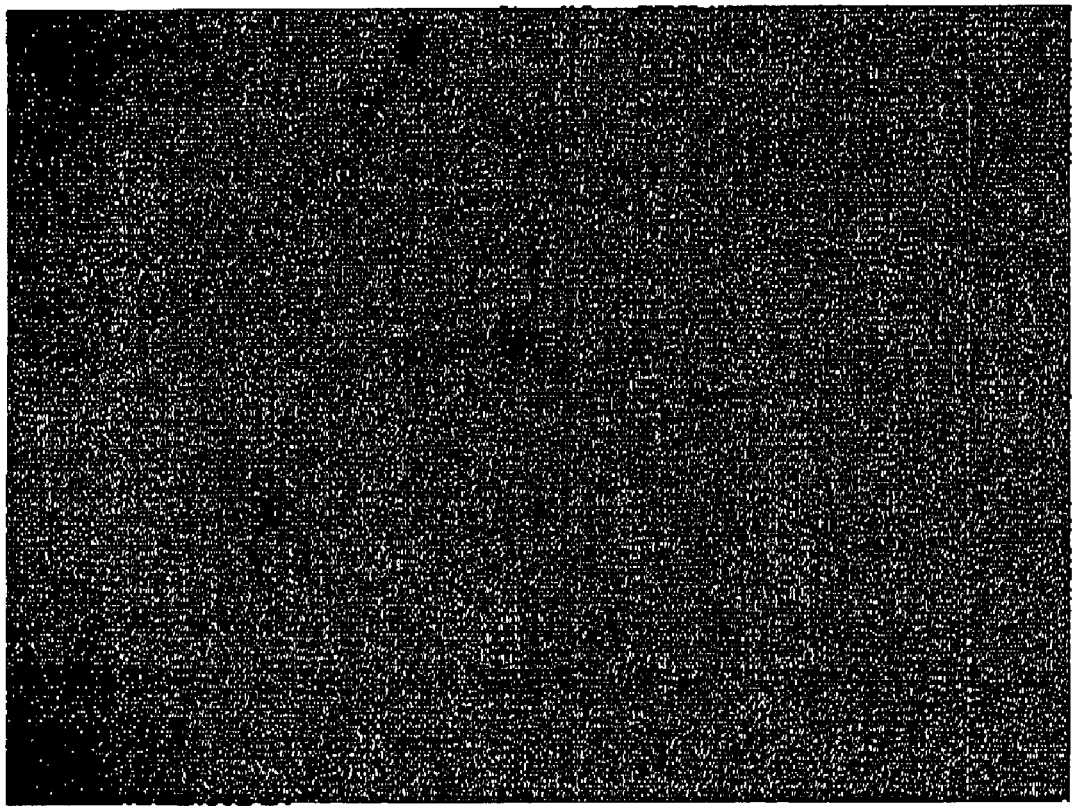
Figure 6:
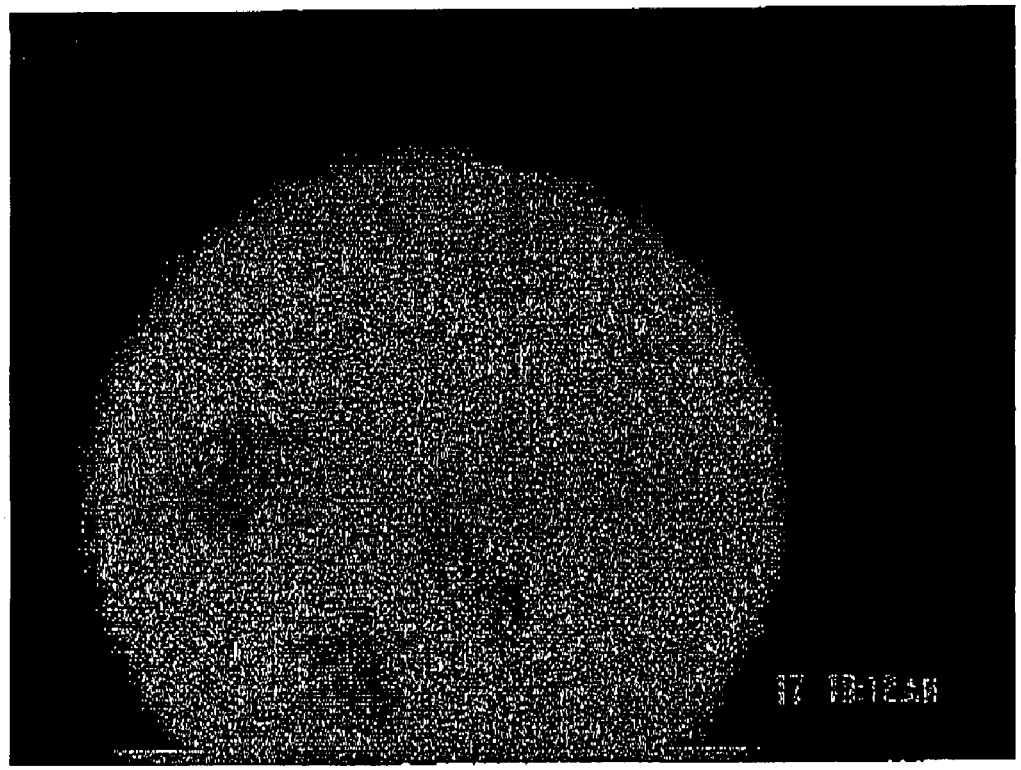

Fragment of mature cartilage with partial hyalinization. (Without evidence of malignant neoplasia). See confirmation in the image of FIG. 4.

Discussion of the results obtained

The functional result subsequent to the implantation of the product was very satisfactory for most of treated patients. The difference between the plain systemic drug management and the intraarticular application of the chondroitin sulfate and sodium hyaluronate implant is very evidently in favor of the latter. It must be considered that the plain intraarticular rheological change (viscosity, elasticity and plasticity) reduces the pain and stimulates a synovial response, changing the viscoelastic features of the fluid. However, the basic difference lies in the medium and long term response which may be effected by the chondrogenic induction provoked by CS and, with it, the permanent solution to the chondral lesion, to the clinical manifestations and the functional disability, as well as to the risk of major surgery.

Conclusions:

The treatment of osteochondral lesions with intraarticular sodium chondroitin sulfate and sodium hyaluronate has proven to have a significantly favorable clinical response compared with the conventional treatment. This response has been confirmed with pre- and posttreatment arthroscopic imaging, conventional and electron microscope examination as well as histophysiology testing (POSITIVE S-100 Protein) showing that the damaged cartilage is regenerated in a period of about 2 years recovering its normal structure and function. The indications for the chondrogenic induction intraarticular treatment are preferably addressed to patients with chondromalacia and grades I and II osteoarthritis in any joint of the human body.

The original cause of the osteochondral pathology should invariably be treated, as the long-term result of the procedure will depend on that. Prior surgical management, where indicated, through minimal invasive surgery, is an excellent alternative for the integral management of osteochondral lesions and their better long-term prognosis.

Similarly, the methods of the present invention may be used in conjunction with other known therapies. For example, the chondroitin sulfate-hyaluronate mixture of the present invention may be administered to a joint in need thereof in combination with one or more other agents selected from antiinflammatories, antirheumatics, steroids and chondrogenic stimulating factors, either separately or in a single formulation.

Therefore, the mixture of sodium hyaluronate and sodium chondroitin sulfate can be used now in defined amounts in a therapeutically useful manner for all the characterized pathological conditions by the simple intrarrticular application route, and the absence of risks of both components makes this therapy particularly attractive.

As previously discussed, the viscoelastic compositions of the present invention are known to have utility in ophthalmic surgery. Those skilled in the viscoelastic arts will appreciate, however, that such compositions will have utility beyond ophthalmic and joint therapy as described above. They may be used in a variety of therapies, and especially in drug delivery, cosmetic surgery and reconstructive surgery. The compositions of the present invention are well suited for delivery of anti-fibrotics, antibiotics, steroidal and non-steroidal antiinflammatories, anesthetics, analgesics and other medicaments or gene therapies to diseased or traumatized tissues in need thereof. Cosmetically, there compositions may be injected to reduce wrinkles or to treat varicose veins. For treatment of dermal lines or wrinkles, these compositions may combined with a muscle relaxing agent such as botulinum toxin type A, commercially available as BOTOX® (Allergan, Inc., Irvine Calif., USA), and injected subdermally in the conventional manner. The presently disclosed compositions and methods may also be used in any environment where there is a need for tissue separation or stabilization and the potential exists for complications, typically post-surgical, arising from tissue fibrosis and/or adhesions. They will be particularly useful in nasal, spinal cord, cardiovascular, orthopoedic and orthodontic surgical procedures that would otherwise be prone to such complications.

Those skilled in the art will recognize that the preferred modes may be altered or amended without straying away from the true spirit and scope of the invention as defined in the enclosed claims.

What is claimed is:

1. A therapeutic method for the treatment of a joint exhibiting degeneration of articular cartilage comprising the intraarticular administration to said joint of a viscous composition comprising a therapeutically effective amount of a mixture of chondroitin sulfate and hyaluronic acid or pharmaceutically acceptable salts thereof.

2. The method of claim 1, wherein the joint is in a human patient and the degeneration of the cartilage is caused by chondrmalacia or osteoarthritis of grade I or grade II.

3. The method of either claim 1 or claim 2, wherein the composition comprises a mixture of chondroitin sulfate at a concentration of 0.1 to 50% by weight and sodium hyaluronate at a concentration of 0.1 to 50% by weight.

4. The method of claim 3, wherein the chondroitin sulfate concentration is from 0.1 to 5.3% by weight and the sodium hyaluroante concentration is from 0.1 to 4.2% by weight of the composition.

5. The method of claim 4, wherein the composition is a sterile, non-pyrogenic, viscoelastic solution comprising a mixture of chondroitin sulfate and sodium hyaluronate in a ratio of about 4 parts by weight chondroitin sulfate to about 3 parts by weight sodium hyaluronate.

6. The method of claim 5, wherein the concentration of chondroitin sulfate is about 40 mg/ml and the concentration of sodium hyaluronate is about 30 mg/ml.

7. The method of claim 6, wherein the chondroitin sulfate has a molecular weight of 20,000 to 50,000 daltons, the sodium hyaluronate has a molecular weight of 500,000 to 1,000,000 daltons, and the composition has a viscosity of 20,000 to 60,000 cps.

8. The method of claim 1, wherein one or more doses of between 0.5 and 1.5 cubic centimeters of the viscoelastic composition are administered to the affected joint.

9. The method of claim 8, wherein 2 to 6 doses of the viscoelastic composition are administered over 1 to 3 months.

10. The method of claim 9, wherein 2 to 4 doses of the viscoelastic composition are administered at 10 to 20 day intervals.

11. The method of claim 10, wherein 3 doses of the viscoelastic composition are administered at 15 day intervals.

12. The therapeutic method according to claim 8, wherein the joint is a human joint selected from the group formed by the following joints: i) knees, shoulders and sacroiliac; ii) coxofemoral, ankles and elbows; and iii) interphalangeal and wrists.

13. The therapeutic method according to claim 12, wherein each dose of the viscoelastic composition is 1.5 cubic centimeters of the composition for the knee, shoulder or sacroiliac joints.

14. The therapeutic method according to claim 8, wherein each dose of the viscoelastic composition is 0.75 cubic centimeters of the composition for the coxofemoral, ankle or elbow joints.

15. The therapeutic method according to claim 8, wherein each dose of the viscoelastic composition is 0.5 cubic centimeters of the composition for the interphalangeal or wrist joints.

16. A method of repairing or regenerating cartilage in a mammalian joint characterized by cartilage degeneration or trauma, comprising the intraaticular administration of a mixture of chondroitin sulfate and hyaluronic acid or pharmaceutically acceptable salts thereof.

* * * * *

UNITED STATES PATENT AND TRADEMARK OFFICE
CERTIFICATE OF CORRECTION

PATENT NO. : 6,949,525 B2
DATED : September 27, 2005
INVENTOR(S) : Elias Humberto Hermida Ochoa It is certified that error appears in the above-identified patent and that said Letters Patent is hereby corrected as shown below:

Title page,
Item [86], change
"§ 371 (c)(1),
 (2), (4) Date: August 27, 2003" to
-- This application is a 371 of PCT/EP02/12703 filed on 11/13/2002; which claims benefit of U.S. application No. 10/082,743 filed on 02/22/2002; which claims benefit of Mexican application No. PA/a/2001/011542 filed on 11/13/2001. --.

Signed and Sealed this

Sixth Day of December, 2005

JON W. DUDAS
*Director of the United States Patent and Trademark Office*